US011426569B2

(12) United States Patent
Chen

(10) Patent No.: US 11,426,569 B2
(45) Date of Patent: Aug. 30, 2022

(54) FLUID PRODUCT APPLICATOR

(71) Applicant: APTAR FRANCE SAS, Le Neubourg (FR)

(72) Inventor: Alexandre Chen, Villenoy (FR)

(73) Assignee: APTAR FRANCE SAS, Le Neubourg (FR)

(*) Notice: Subject to any disclaimer, the term of this patent is extended or adjusted under 35 U.S.C. 154(b) by 283 days.

(21) Appl. No.: 16/764,195

(22) PCT Filed: Nov. 15, 2018

(86) PCT No.: PCT/FR2018/052859
§ 371 (c)(1),
(2) Date: May 14, 2020

(87) PCT Pub. No.: WO2019/097173
PCT Pub. Date: May 23, 2019

(65) Prior Publication Data
US 2020/0384251 A1    Dec. 10, 2020

(30) Foreign Application Priority Data

Nov. 16, 2017 (FR) ...................................... 1760812

(51) Int. Cl.
*A61M 35/00* (2006.01)
*A61B 90/00* (2016.01)
(Continued)

(52) U.S. Cl.
CPC ........... *A61M 35/003* (2013.01); *A45D 34/04* (2013.01); *A61B 5/0531* (2013.01); *A61B 90/06* (2016.02);
(Continued)

(58) Field of Classification Search
CPC .... A61M 35/003; A45D 34/04; A61B 5/0531; A61B 90/06; A61B 2090/065;
(Continued)

(56) References Cited

U.S. PATENT DOCUMENTS 6,253,133 B1* 6/2001 Sakai ................ B60R 21/01532
180/268
2009/0287195 A1* 11/2009 Altshuler .................. A61F 7/02
606/9

(Continued)

FOREIGN PATENT DOCUMENTS

WO        2013/121145 A1    8/2013

OTHER PUBLICATIONS

International Search Report of PCT/FR2018/052859 dated Feb. 11, 2019 [PCT/ISA/210].

(Continued)

*Primary Examiner* — Jonathan T Kuo
(74) *Attorney, Agent, or Firm* — Sughrue Mion, PLLC

(57) ABSTRACT

A fluid applicator including a skin contact detector device. The contact detector device includes a flexible outer substrate (S1) that defines an outer contact surface (S11), the flexible outer substrate (S1) covering a detection zone (Z) that has a plurality of conductive pellets (P1, P2, P3, P4, P5) separate from one another, the conductive pellets (P1, P2, P3, P4, P5) being arranged above a common conductive plate (D). The conductive pellets (P1, P2, P3, P4, P5), in the absence of stress, are spaced apart from the common conductive plate (D) by insulating spacers (C), so that pressure exerted on the flexible outer substrate (S1) causes at least one of the conductive pellets (P1, P2, P3, P4, P5) to come into contact with the common conductive plate (D), thereby creating at least one short-circuit signal.

13 Claims, 3 Drawing Sheets

(51) Int. Cl.
*A45D 34/04* (2006.01)
*A61B 5/0531* (2021.01)
*A61N 5/06* (2006.01)
*G01L 1/20* (2006.01)

(52) U.S. Cl.
CPC ............ *A61N 5/0616* (2013.01); *G01L 1/205* (2013.01); *A61B 2090/065* (2016.02); *A61B 2562/166* (2013.01)

(58) Field of Classification Search
CPC ........ A61B 2562/166; A61B 2562/046; A61B 2562/125; A61B 5/6844; A61N 5/0616; G01L 1/205
See application file for complete search history.

(56) References Cited

U.S. PATENT DOCUMENTS

2010/0090299 A1\* 4/2010 Chang ................... G01L 1/205
257/419
2014/0296772 A1\* 10/2014 Duquet ............... A61N 5/0616
604/20
2015/0059486 A1 3/2015 Choong et al.

OTHER PUBLICATIONS

International Preliminary Report on Patentability with a Translation of Written Opinion in International Application No. PCT/FR2018/052859, dated May 28, 2020.

\* cited by examiner

FLUID PRODUCT APPLICATOR

CROSS REFERENCE TO RELATED APPLICATIONS

This application is a National Stage of International Application No. PCT/FR2018/052859, filed Nov. 15, 2018, claiming priority to French Patent Application No. 1760812, filed Nov. 16, 2017.

The present invention relates to a fluid applicator including a contact detector device for detecting contact with the skin, and in particular direct or indirect contact. Advantageous fields of application of the invention are thus the fields of cosmetics and pharmacy, and more particularly the field of fluid applicators for applying fluid, such as cream, pomade, gels, etc. However, other fields of application in which extended contact is used are not excluded.

In the prior art, document WO 2013/121145 is already known, which describes a fluid dispenser comprising a fluid reservoir, a fluid dispenser member that is connected to the reservoir, an actuator member for actuating the dispenser member, a fluid dispenser orifice that is connected to the dispenser member, and an applicator surface for applying the fluid coming from the dispenser orifice onto the skin. The dispenser further comprises at least one source of radiation, such as a light-emitting diode (LED), having an anti-inflammatory action and/or a stimulating action for stimulating skin-regeneration metabolisms. More generally, that document describes a fluid dispenser/applicator that incorporates activator means for activating the fluid and/or the skin.

With such a fluid dispenser/applicator, it can be advantageous to know when the applicator surface coated in fluid is effectively and/or correctly in contact with the skin, so as to be able to activate the source of radiation. Specifically, it is necessary to avoid the radiation from the source being directed towards sensitive organs, such as the eyes or the mucous membranes. To do this, various detection techniques have already been tested, e.g. IR detection, ambient condition sensors, mechanical contactors, micro-currents, etc. However, the results are not sufficiently effective and reliable, in particular as a result of the presence of fluid between the applicator surface of the applicator and the skin, which disturbs detection.

In addition, the resistive touch screens of smartphones could be suitable as contact detectors, but it is not possible to have a diagonal of less than 1.7 inches (") and to detect a plurality of contact zones at the same time.

One of the objects of the present invention is thus to remedy the above-mentioned drawback of the prior art by developing a novel detector device that is sensitive to the presence of fluid. Another object of the invention is to detect contact over an extended zone or area, so as to avoid localized or spot contact detection. Still another object is to develop a detector device that can be used with sources of radiation, without disturbing them or attenuating them significantly. Another object is to detect contact with the skin (with or without cream) on a transparent support. Still another object is to develop a detector device that is proof against the fluid.

To achieve these objects, the present invention proposes a fluid applicator including a contact detector device for detecting contact, and in particular contact with the skin, the contact detector device including a flexible outer substrate that defines an outer contact surface, the flexible outer substrate covering a detection zone that comprises a plurality of conductive pellets that are separate from one another, the conductive pellets being arranged above a common conductive plate, the conductive pellets, in the absence of stress, being spaced apart from the common conductive plate by insulating spacers, so that pressure exerted on the flexible outer substrate causes at least one of the conductive pellets to come into contact with the common conductive plate, thereby creating at least one short-circuit signal.

Each conductive pellet can thus create contact, and thus a short circuit, with the underlying common plate. The aim is not to locate the position of the pellet where contact has been created, as with a touch screen for a smartphone or a computer, but merely to observe that a short circuit has been generated via a determined pellet. This observation is purely binary: short circuit or not via a pellet.

By identifying or discriminating each pellet in unique manner, it is thus possible to identify accurately which pellet(s) is/are in contact with the common plate.

In addition, as a function of the number of pellets in which a short circuit is observed at any one moment, it is possible to deduce therefrom that the contact is extensive to a greater or lesser extent.

It is thus possible to say that the contact detector device of the invention makes it possible not only to detect any contact in its detection zone, but also to determine the extent or the magnitude of the contact in terms of surface area. This gives additional or complementary information that can be used to generate subsequent actions.

In addition, as a result of cutting or segmenting the detection zone into a plurality of sub-zones defined by the conductive pellets, it is also possible to map accurately the location of the extended contact as a function both of the number of short-circuited pellets, and also of their positions. In this way, it is possible to plot a pattern of the extended contact on the detection zone.

It is also possible to measure the duration of each short circuit and to correlate the lifespans of all of the pellets, so as to deduce therefrom which pellets are short circuited the most, and this provides information about the position where contact is most frequently made.

It goes without saying that the contact detector device of the invention may be used in any application that requires contact detection, ranging from mere detection of the presence of a contact to thorough analysis of the identity of the contact, of the location of the contact, of the duration of the contact, and of the extent of the contact According to an advantageous characteristic, at least one of the conductive pellets and of the insulating spacers is flexible. In other words, the pellets may be flexible or the spacers may be flexible or both the pellets and the spacers may be flexible. In practice, the pellets are flexible since they are very thin, and they are mounted on the flexible outer substrate, and the spacers are hard since they are made of resin, and they are applied on the common plate, which is advantageously mounted on a rigid base substrate. Thus, the flexible outer substrate is deformed by contact with an external body, such as the skin, such deformation affecting the pellets, some or all of which come into contact with the rigid common plate, thereby creating one or more short circuits.

In an advantageous aspect of the invention, the detector device may be associated with processing software that delivers an extended-contact signal when it receives some threshold number of short-circuit signals, the threshold number being at least equal to one and at most equal to the number of conductive pellets. When the threshold number is one, it is possible to select the central pellet, for example. By way of example, a threshold number of two pellets could be selected. Those two pellets may be adjacent or spaced apart a little so as to detect a contact of small extent or, on the contrary, they may be spaced apart so as to detect a contact of greater extent.

Advantageously, the outer contact surface presents a profile other than plane, in particular a curved profile. This is possible given that the outer substrate is flexible, and that it is not necessary to detect the precise position of the contact generating the short circuit.

In addition, the detector device is transparent to electromagnetic radiation and to heat. Thus, it can be used in dispensers/applicators that generate electromagnetic radiation and/or heat, the detector device having radiation and/or heat passing therethough without creating significant losses or disturbances.

According to another characteristic of the invention, the detection zone presents a total surface area lying in the range about 300 square millimeters ($mm^2$) to about 400 $mm^2$, with conductive pellets of less than 100 $mm^2$. In comparison, a conventional touch screen measures more than 600 $mm^2$.

The present invention defines a fluid applicator including a detector device as defined above. In an embodiment, the outer contact surface forms a fluid applicator surface for applying fluid onto a target surface, such as the skin. In a variant, the applicator includes a fluid applicator wall that is arranged in contact with the outer contact surface.

Advantageously, the applicator includes an activation source for activating the fluid and/or the skin, and integrated or exposed processing software that receives the short-circuit signals and processes them so as to obtain at least some of the following information:
  the identities of the short-circuited conductive pellets;
  the locations of the short-circuited conductive pellets in the detection zone;
  the number of conductive pellets that are short circuited simultaneously;
  the duration of the short circuit of each short-circuited conductive pellet; and
  the breaking of the short circuit of each short-circuited conductive pellet;
so as to deduce therefrom at least one of the following actions:
  triggering the activation source whenever a threshold number of simultaneous short-circuit signals is detected, and advantageously for a fixed period of time;
  interrupting the activation source whenever a threshold number of simultaneous short-circuit signals is no longer detected; and
  displaying on a screen, such as a smartphone, information relating to the identities, the locations, the number, and/or durations of the short circuits, e.g. in the form of a virtual representation of the detection zone with its conductive pellets.

It can thus be seen that the detector device of the invention finds an advantageous application in a fluid applicator, since it makes it possible not only to control the activation source, but also to inform the user about how to use the applicator. The user can be warned that the applicator is not being used properly, and solutions can be proposed to the user so as to improve its use. The detector device of the invention thus constitutes a genuine source of varied and wide-ranging information that can be processed by means of appropriate software so as to deliver refined data to the applicator and/or to the user.

The invention can also be applied to a fluid dispenser including a cap, the presence and/or absence of which is detected by the detector device of the invention. It can also be applied to a fluid dispenser that includes a squeezable reservoir, the hand pressure being exerted by the user on the squeezable reservoir being perceived by the detector device of the invention. It can clearly be seen that the detector device of the invention can be used in a wide variety of applications.

The invention is described below in greater detail with reference to the accompanying drawings, which show an embodiment of the invention by way of non-limiting example and its implementation in a fluid dispenser/applicator.

Reference is made firstly to FIGS. 1 to 4 in order to describe the structure and the operation of the contact detector device of the invention in a non-limiting embodiment.

The contact detector device comprises a base substrate S2, a common conductive plate D, insulating spacers C, a plurality of conductive pellets P1, P2, P3, P4, and P5, and an outer substrate S1.

Figure 1:
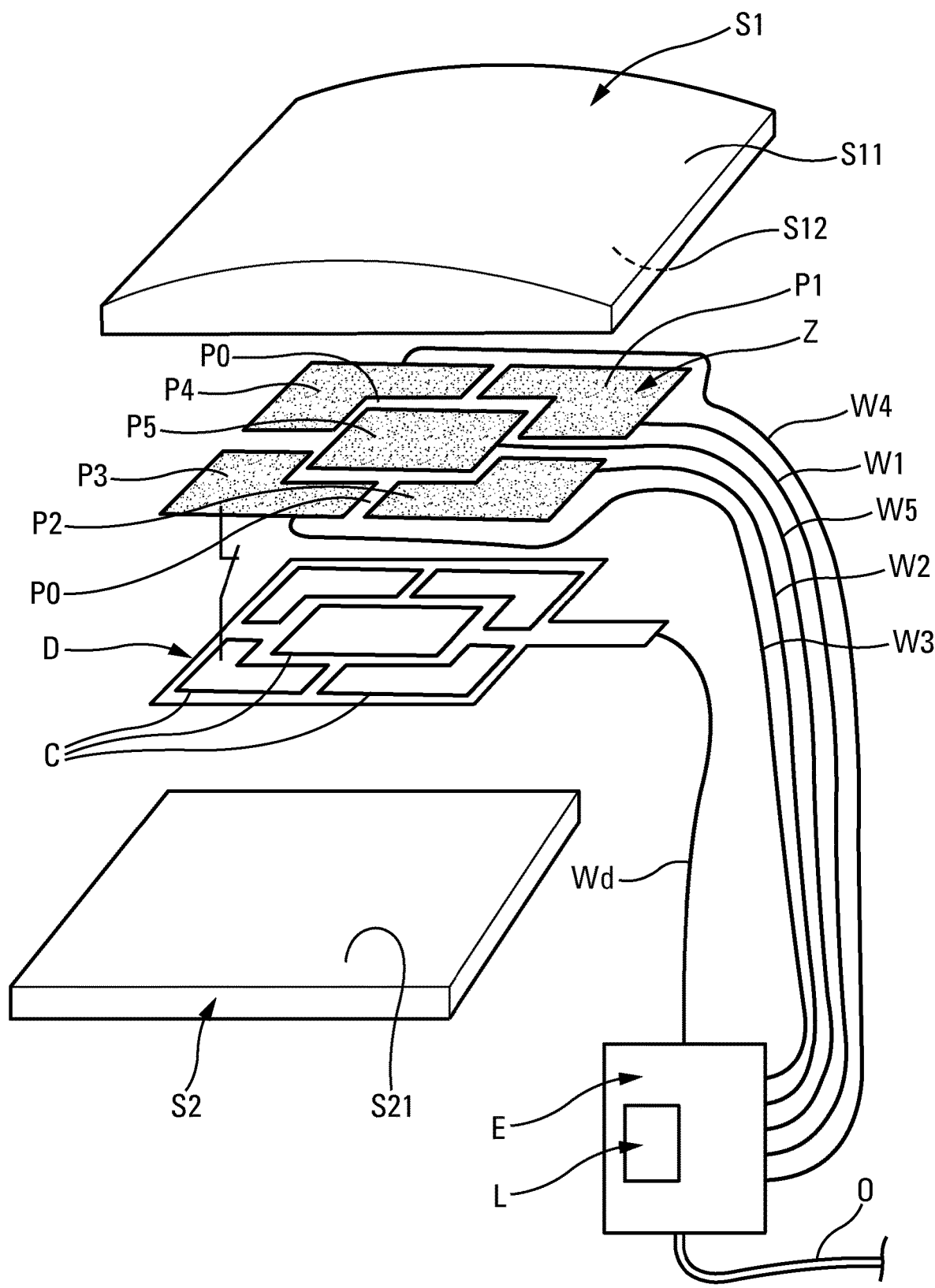
FIG. 1 is an exploded diagrammatic perspective view of the contact detector device of the invention.

The base substrate S2 is not really critical to the present invention, and it may be constituted by any appropriate support. In some circumstances, the base substrate S2 may even be considered as forming part of another device or assembly. The base substrate S2 is made out of a material that is insulating or not very conductive, and that is preferably rigid. The material may be a plastics material, e.g. a transparent thermoplastic polymer, such as Plexiglass®. The base substrate S2 defines a support surface S21 that may be plane, as can be seen in FIG. 1, or it need not be plane: e.g. it may be curved or domed. The thickness of the base substrate S2 may be constant, as can be seen in FIG. 1, or, on the contrary, it may vary. The base substrate S2 may present both a thickness that is constant and also a shape that is curved or rounded. It may even present a complex shape that is not geometrical.

The outer substrate S1 may be made out of any material that is insulating or not very conductive, and that presents flexibility or springiness having shape memory related the force exerted by the contact to be detected. Its thickness is also determined as a function of the force exerted by the contact to be detected. The outer substrate S1 is preferably transparent to electromagnetic radiation and/or to heat. The material may be a plastics material, e.g. polyethylene terephthalate (PET). The outer substrate S1 defines an outer contact surface S11 that may be plane, or that need not be plane: e.g. it may be curved or domed, as can be seen in FIG. 1. The outer substrate S1 also defines a mounting surface S12 that is remote from the outer contact surface S11. The mounting surface S12 is preferably plane. The thickness of the outer substrate S1 may be constant, or, on the contrary, it may vary, as can be seen in FIG. 1. The outer substrate S1 may present both a thickness that is constant and also a shape that is curved or rounded. It may even present a complex shape that is not geometrical.

The common conductive plate D is single unit, i.e. made as a single piece or from a plurality of touching parts. It is preferably plane, like the support surface S21, but it could equally be curved, domed, concave, or of a complex shape that is not geometrical. In FIG. 1, the common conductive plate D presents a shape that is generally square or rectangular. Other shapes, optionally-geometrical shapes, are possible. The common conductive plate D is made out of a material that is electrically conductive. In practice, it may be formed by depositing a thin layer of metal oxide, such as indium tin oxide, on the support surface S21, with a thickness lying in the range about 5 micrometers ($\mu m$) to about 100 $\mu m$, advantageously in the range about 5 $\mu m$ to about 10 $\mu m$, and preferably being 5 $\mu m \pm 1$ $\mu m$. The thinner the layer, the more it is transparent.

The conductive pellets are five in number and they are referenced P1, P2, P3, P4, and P5 in the figures. Naturally, the number is not limiting, and it may vary from one to infinity. In practice, it is possible to envisage 2 to 100 pellets, advantageously 4 to 20 pellets. They are preferably plane, like the mounting surface S12, but they could equally be curved, domed, concave, or of a complex shape that is not geometrical.

The conductive pellets are made out of a material that is electrically conductive. In practice, they may be formed by depositing a thin layer of metal oxide, such as indium tin oxide, on the mounting surface S12, with a thickness lying in the range about 5 $\mu m$ to about 100 $\mu m$, advantageously in the range about 5 $\mu m$ to about 10 $\mu m$, and preferably being 5 $\mu m \pm 1$ $\mu m$. The thinner the layer, the more it is transparent.

In FIG. 1, it can be seen that the conductive pellets P1, P2, P3, P4, and P5 present a shape that is generally square or rectangular, with the pellets spaced apart from one another by narrow areas P0. Together the pellets form a detection zone Z having a surface area that is less than or equal to the surface area of the common conductive plate D. In the figure, there are four peripheral pellets P1, P2, P3, and P4 that are right-angle shaped or L-shaped and a central pellet P5 that is square or rectangular shaped. The areas P0 form a central frame of square or rectangular shape, with four branches that start from the middle of each side of the central frame. The width of the areas P0 is substantially constant.

Figure 2:
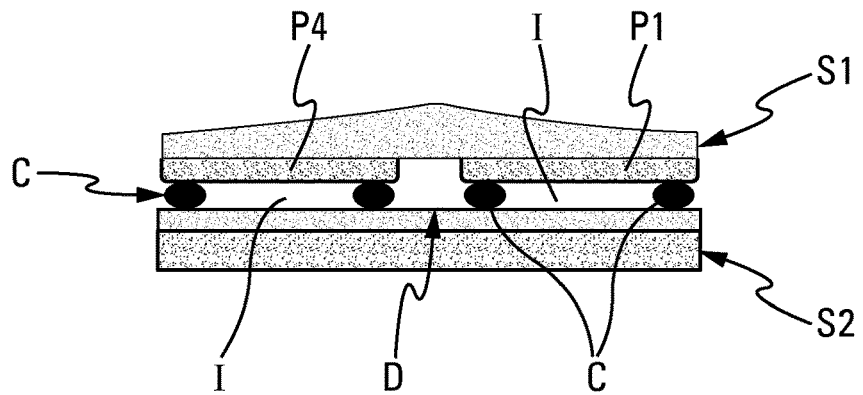
FIG. 2 is a vertical section view through the contact detector device, in its rest state.

In FIG. 2, it can be seen that the conductive pellets P1 and P4 are spaced apart from the common conductive plate D by spacers C, so as to form between them gaps I. The spacers C are made out of an insulating material, such as a resin, that may be applied on the common conductive plate D, as shown in FIG. 1, in which it is possible to see five resin frames having shapes that are identical to the shapes of the respective conductive pellets P1 to P5. In a variant, the spacers C may be deposited on the conductive pellets. The thickness of the spacers C lies in the range about 5 $\mu m$ to about 30 $\mu m$, advantageously in the range about 10 $\mu m$ to about 20 $\mu m$, and is preferably 5 $\mu m \pm 2$ $\mu m$. The gaps I present a thickness related to the thickness of the spacers C: the thickness of the gaps may be a little less than the thickness of the spacers, e.g. lying in the range about 1 $\mu m$ to about 3 $\mu m$, as a result of the deformability of the outer substrate S1 and of the pellets P1 to P5.

Figure 4:
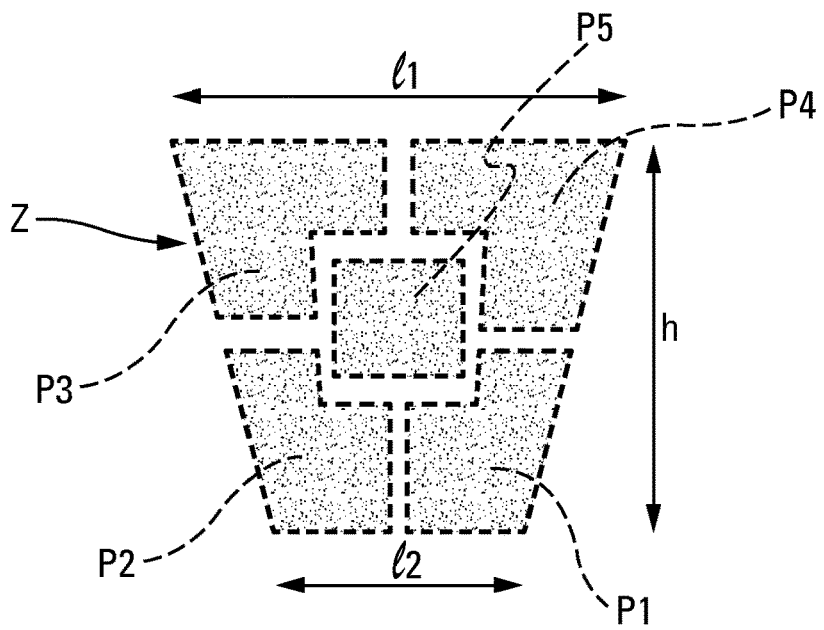
FIG. 4 is a very diagrammatic view showing a detection zone of trapezoidal shape.

The size of the detection zone Z may be relatively small compared to the conventional touch screens of smartphones. It may present sides that are shorter than 20 millimeters (mm), corresponding to a total surface area of less than 400 $mm^2$. FIG. 4 shows a detection zone Z that is particular, in the sense that it is not of square or rectangular shape, but of trapezoidal shape, with a top side having a width 1 1 of 20 mm, and bottom side having a width 1 2 of 15 mm, and a height h of 20 mm. With these dimensions, each pellet presents a surface area that is less than 100 $mm^2$, and some are even less than 60 $mm^2$.

Finally, wires, cables, or conductive tracks W1 to W5 connect each of the pellets P1 to P5 respectively to electronic processing and control means E that advantageously incorporate processing software L. A wire, cable, or conductive track Wd of the same type connects the common conductive plate D to the electronic processing and control means E.

FIG. 2 shows the contact detector device at rest, i.e. when it is not subjected to any external stress. The conductive pellets P1 and P4 are spaced apart from the plate D by the spacers C that create gaps I. A voltage is applied between the pellets and the plate: nothing happens given that there is no contact.

Figure 3:
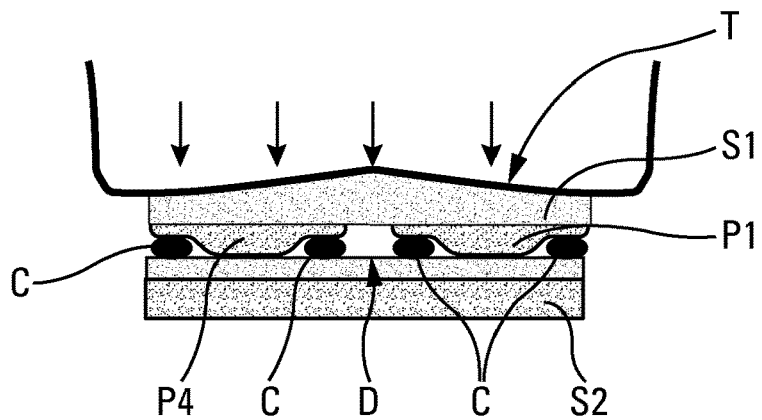
FIG. 3 is a view similar to the view in FIG. 2 for the contact detector device, in its stressed state.

In FIG. 3, the outer substrate S1 is now in contact with an external body T that may be the skin of a user. The body T exerts a pressure on the outer substrate S1 such that it deforms, along with the conductive pellets P1 and P4 that thus come into contact with the plate D, creating two short circuits.

What occurs at the pellets P1 and P4 is also valid for the other pellets P2, P3, and P5. Each of the short circuits created generates a short-circuit signal that is sent to the electronic processing and control means E.

Figure 5:
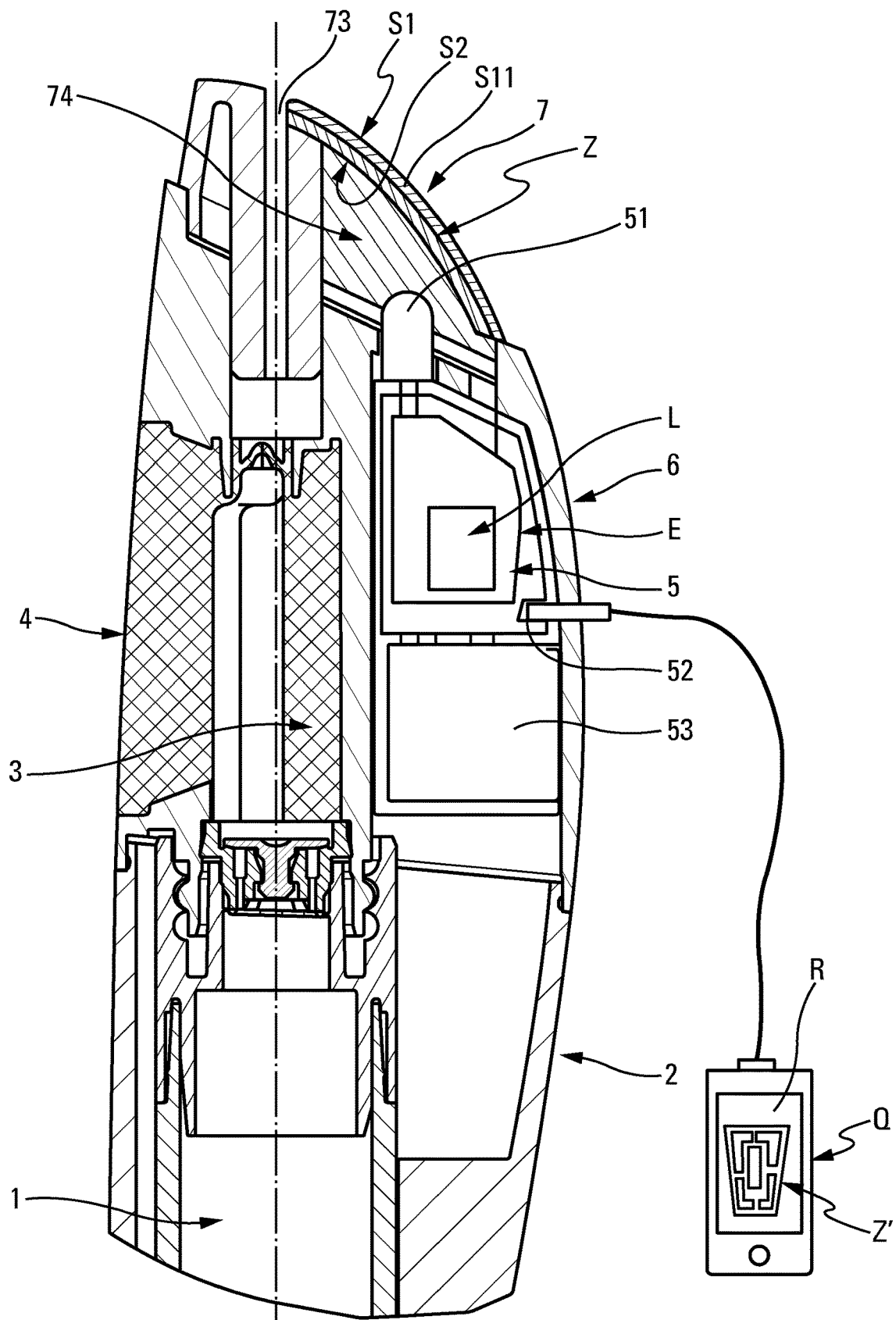
FIG. 5 is a vertical section view through a fluid dispenser/applicator incorporating the contact detector device of the invention.

Reference is made below to FIG. 5 in order to see how the contact detector device of the invention can be used in a fluid dispenser/applicator. The dispenser/applicator comprises: a fluid reservoir 1; a casing 2 in which the reservoir 1 is received; a dispenser member 3, specifically a pump; an actuator member 4 for actuating the pump 3, and that is specifically incorporated in the pump; a module 5 that is provided with one (or more) sources of radiation 51; a body 6 that receives the pump 3, the actuator member 4, and the module 5; and finally a dispenser head 7 that is mounted on the body 6. The head 7 forms a dispenser orifice 73 and a fluid applicator surface. It is also provided with a waveguide 74 (e.g. a lens) for guiding, amplifying, or focusing the light emitted by the source of radiation 51. Optionally, the dispenser may also include a protective cap that covers the dispenser head 7. With the exception of the module 5, all of the component elements of the dispenser may be made by injection-molding plastics material. It should be understood that it is possible to dispense fluid through the dispenser orifice 73 in the applicator surface by actuating the actuator member 4 of the dispenser member 3 that makes it possible to take the fluid from the reservoir 1 and to force it through the dispenser orifice 73. Once the dispensed fluid is present on the applicator surface, the user may apply it and spread it over a target surface, such as the skin. The dispensed fluid is preferably a viscous fluid, such as a cream, a gel, a pomade, etc.

The module 5 may be in the form of a small case that has one or more LEDs on top, as a source of radiation 51. The module includes power supply means 53, e.g. in the form of a battery, and electronic processing and control means E that, by way of example, may be mounted on a small printed circuit board. The electronic means advantageously incorporate processing software L. Naturally, the module 5 may also incorporate other electronic components that are capable of performing other functions. The module 5 also includes a port 52, e.g. a USB port, for connecting to a smartphone or a computer.

Without going beyond the ambit of the invention, instead of the LED(s), it is possible to provide other sources of activation that act on the fluid and/or on the tissue (skin). Inter alia, mention can be made of: all forms of (optionally visible) electromagnetic radiation; heat sources; vibration; electric currents (e.g. iontophoresis); etc.

The contact detector device of the invention is incorporated in the applicator in the dispenser head 7. In greater detail, the applicator surface, at least in its portion situated to the right of the dispenser orifice 73 in FIG. 5, is formed by the outer contact surface S11 of the outer substrate S1 of the contact detector device of the invention. Below the substrate S1 there are situated the detection zone Z with its conductive pellets, then the common plate D that is mounted together with its spacers E on the base substrate S2. In FIG. 5, it should be observed that the contact detector device is curved or rounded in its entirety, with wall thicknesses that are constant.

In a variant that is not shown, the outer contact surface S11 could be covered by a fluid applicator wall that is formed by the head 7. The wall could be flexible. It could also be rigid: it could thus be mounted in floating manner on the outer contact surface S11.

When a user wishes to use the dispenser/applicator, the user begins by actuating the pump 3 by pressing on the pusher 4, with the dispenser orifice 73 positioned in the proximity of its target (skin), so as to deposit a dose of fluid thereon. Then, the user uses the outer contact surface S11 to spread the fluid over the target. It is at this moment that the contact detector device of the invention comes into play. The short-circuit signals generated by contact between the pellets and the plate, as a result of the pressure force exerted on contact with the skin, are sent to the processing software L which processes them so as to obtain information, including the following:

the identities of the short-circuited conductive pellets;
the locations of the short-circuited conductive pellets in the detection zone;
the number of conductive pellets that are short circuited simultaneously;
the duration of the short circuit of each short-circuited conductive pellet; and
the breaking of the short circuit of each short-circuited conductive pellet.

The information can then be correlated so as to deduce therefrom at least one of the following actions:

triggering the power supply of the source of radiation 51 whenever a threshold number of simultaneous short-circuit signals is detected, and advantageously for a fixed period of time;
interrupting the power supply of the source of radiation 51 whenever a threshold number of simultaneous short-circuit signals is no longer detected; and
displaying on a screen R, such as a smartphone Q, information relating to the identities, the locations, the number, and/or durations of the short circuits, e.g. in the form of a virtual representation Z' of the detection zone Z with its conductive pellets P1 to P5.

Triggering and interrupting the power supply of the source of radiation 51 are internal actions that have a direct influence on the operation of the dispenser/applicator, for the purpose of ensuring that the source of radiation 51 is triggered only when the outer contact surface S11 is in contact with the user's skin, and is stopped as soon as the surface S11 is removed from the skin. This makes it possible to avoid the source of radiation 51 being directed towards sensitive tissues, such as the eyes and/or the mucous membranes. The threshold number of short-circuit signals may be varied and can lie in the range one to the total number of pellets in the detection zone Z, it being understood that, in theory, the number is not limited.

The other actions are external in the sense that they can be used by the user to monitor the progress of fluid application, either in real time, or from a recording. The user can use the processed information displayed on the screen R of a smartphone Q to correct faults in handling the dispenser/applicator and thus improve performance. For example, if the user sees that some pellets are nearly always short circuited while others are almost never short circuited, the user can try to modify the way the dispenser/applicator is oriented relative to the target so as to make contact more uniform or so as to extend it to the pellets that are little used. The screen R of the smartphone Q can thus become the member for controlling the dispenser/applicator in real time.

The processing software L can be loaded in its entirety in the dispenser/applicator, advantageously in its module 5. In a variant, a portion of the processing software L could be external, e.g. in the form of an application loaded into the smartphone Q.

The contact detector device of the invention could also be used in other items or articles, e.g. for detecting the presence of a member defining an extended contact zone. The presence of a cap or of a cover defining an annular contact zone could be detected, the cap or the cover being a part of a fluid dispenser, for example. A squeezable reservoir of a fluid dispenser being held in the hand could also be detected by means of the contact detector device of the invention. Naturally, the invention finds an advantageous application wherever it is desired to have contact over an extended area. However, spot or narrow contact may be detected quite reliably with the invention.

In all circumstances, the contact detector device of the invention delivers basic information that results directly from the various conductive pellets P1 to P5 being short circuited: identity, number and location of the short-circuited pellets; start time, duration, and end time of the short circuit. The basic information is collected by the electronic processing and control means E, and more particularly by the software L, which correlates it and processes it so as to extract therefrom the processed complex information that is used to generate internal actions that control the operation of an appliance (a dispenser or some other appliance) and external actions for use by the user, which could be used to increase the performance of the appliance provided with the contact detector device of the invention.

The invention claimed is:

1. A fluid applicator including a contact detector device for detecting direct or indirect contact with skin, the applicator being characterized in that the contact detector device includes a flexible outer substrate (S1) that defines an outer contact surface (S11), the flexible outer substrate (S1) covering a detection zone (Z) that comprises a plurality of conductive pellets (P1, P2, P3, P4, P5) that are separate from one another, the conductive pellets (P1, P2, P3, P4, P5) being arranged above a common conductive plate (D), the conductive pellets (P1, P2, P3, P4, P5), in the absence of stress, being spaced apart from the common conductive plate (D) by insulating spacers (C), so that pressure exerted on the flexible outer substrate (S1) causes at least one of the conductive pellets (P1, P2, P3, P4, P5) to come into contact with the common conductive plate (D), thereby creating at least one short-circuit signal.

2. An applicator according to claim 1, wherein at least one of the conductive pellets (P1, P2, P3, P4, P5) and of the insulating spacers (C) is flexible.

3. An applicator according to claim 1, wherein the common conductive plate (D) is mounted on a rigid base substrate (S2).

4. An applicator according to claim 1, wherein the outer contact surface (S11) presents a profile other than plane.

5. An applicator according to claim 4, wherein the profile is a curved profile.

6. An applicator according to claim 1, characterized in that it is transparent to electromagnetic radiation and to heat.

7. An applicator according to claim 1, wherein the detection zone (Z) presents a total surface area lying in the range about 300 mm$^2$ to about 400 mm$^2$, with conductive pellets (P1, P2, P3, P4, P5) of less than 100 mm$^2$.

8. An applicator according to claim 1, wherein the outer contact surface (S11) forms a fluid applicator surface for applying a fluid on a target surface.

9. An applicator according to claim 1, including a fluid applicator wall that is arranged in contact with the outer contact surface.

10. An applicator according to claim 1, including an activation source (51) for activating a fluid and/or the skin, and integrated or exposed processing software (L) that receives the at least one short-circuit signal and processes them so as to obtain at least some of the following information:
   the identities of the short-circuited conductive pellets (P1, P2, P3, P4, P5);
   the locations of the short-circuited conductive pellets (P1, P2, P3, P4, P5) in the detection zone;
   the number of conductive pellets (P1, P2, P3, P4, P5) that are short circuited simultaneously;
   the duration of the short circuit of each short-circuited conductive pellet (P1, P2, P3, P4, P5); and
   the breaking of the short circuit of each short-circuited conductive pellet (P1, P2, P3, P4, P5);
   so as to deduce therefrom at least one of the following actions:
   triggering the activation source whenever a threshold number of simultaneous short-circuit signals is detected, and advantageously for a fixed period of time;
   interrupting the activation source whenever a threshold number of simultaneous short-circuit signals is no longer detected; and
   displaying on a screen (R), information relating to the identities, the locations, the number, and/or durations of the short circuits.

11. An applicator according to claim 9, wherein the processing software (L) delivers an extended-contact signal when it receives some threshold number of short-circuit signals, the threshold number being at least equal to two and at most equal to the number of conductive pellets (P1, P2, P3, P4, P5).

12. An applicator according to claim 10, wherein the screen is a screen on a smartphone.

13. An applicator according to claim 10, wherein the displaying on a screen is in the form of a virtual representation (Z') of the detection zone (Z) with its conductive pellets (P1, P2, P3, P4, P5).

* * * * *